US009554975B2

(12) United States Patent
Newby et al.

(10) Patent No.: US 9,554,975 B2
(45) Date of Patent: Jan. 31, 2017

(54) ALKYL SULFATE FREE AND ORTHOPHOSPHATE FREE DENTIFRICE COMPOSITION COMPRISING FLUORIDE SOURCE AND A SILICA DENTAL ABRASIVE

(75) Inventors: Craig Sinclair Newby, Weybridge (GB); Mark Andrew Nisbet, Weybridge (GB); Katherine Sarah Price, Weybridge (GB)

(73) Assignee: Glaxo Group Limited, Brentford, Middlesex (GB)

( * ) Notice: Subject to any disclaimer, the term of this patent is extended or adjusted under 35 U.S.C. 154(b) by 278 days.

(21) Appl. No.: 11/909,210

(22) PCT Filed: Mar. 17, 2006

(86) PCT No.: PCT/EP2006/002665
§ 371 (c)(1),
(2), (4) Date: Sep. 20, 2007

(87) PCT Pub. No.: WO2006/100071
PCT Pub. Date: Sep. 28, 2006

(65) Prior Publication Data
US 2008/0193391 A1 Aug. 14, 2008

(30) Foreign Application Priority Data

Mar. 21, 2005 (GB) .................................. 0505760.9
Dec. 14, 2005 (GB) .................................. 0525458.6

(51) Int. Cl.
| | |
|---|---|
| *A61Q 11/00* | (2006.01) |
| *A61K 8/21* | (2006.01) |
| *A61K 8/29* | (2006.01) |
| *A61K 8/20* | (2006.01) |
| *A61K 8/25* | (2006.01) |
| *A61K 8/34* | (2006.01) |
| *A61K 8/44* | (2006.01) |

(52) U.S. Cl.
CPC . *A61K 8/20* (2013.01); *A61K 8/21* (2013.01); *A61K 8/25* (2013.01); *A61K 8/29* (2013.01); *A61K 8/345* (2013.01); *A61K 8/442* (2013.01); *A61Q 11/00* (2013.01)

(58) Field of Classification Search
CPC ...... A61Q 11/00; A61K 2300/00; A61K 8/19; A61K 8/21
USPC .......................................................... 424/50
See application file for complete search history.

(56) References Cited

U.S. PATENT DOCUMENTS

| | | | | |
|---|---|---|---|---|
| 4,340,583 | A | | 7/1982 | Wason |
| 4,978,522 | A | * | 12/1990 | Barbera et al. ................. 424/52 |
| 5,560,905 | A | * | 10/1996 | Lukacovic ...................... 424/50 |
| 5,624,906 | A | * | 4/1997 | Vermeer .......................... 514/23 |
| 5,628,985 | A | * | 5/1997 | Stiller et al. .................... 424/49 |
| 5,820,853 | A | * | 10/1998 | Glandorf ......................... 424/52 |
| 5,939,048 | A | * | 8/1999 | Alfano et al. .................. 424/49 |
| 5,958,381 | A | | 9/1999 | Curtis et al. .................... 424/54 |
| 5,993,784 | A | | 11/1999 | Hill ................................. 424/49 |
| 2003/0039617 | A1 | * | 2/2003 | White et al. .................... 424/49 |
| 2003/0124065 | A1 | * | 7/2003 | Majeti et al. ................... 424/49 |
| 2003/0165442 | A1 | * | 9/2003 | Baig et al. ...................... 424/57 |
| 2004/0033205 | A1 | | 2/2004 | Date et al. ...................... 424/53 |
| 2004/0131556 | A1 | | 7/2004 | Alexander et al. ............. 424/49 |
| 2004/0146466 | A1 | | 7/2004 | Baig et al. |
| 2005/0031551 | A1 | * | 2/2005 | Prencipe et al. ................ 424/49 |

FOREIGN PATENT DOCUMENTS

| | | |
|---|---|---|
| EP | 162574 | 4/1985 |
| EP | 0200323 A2 | 3/1986 |
| EP | 278744 | 2/1988 |
| EP | 0 263 638 A | 4/1988 |
| EP | 568160 | 10/1989 |
| EP | 1040819 | 3/2000 |
| EP | 1 459 733 A | 9/2004 |
| EP | 1 476 633 A | 11/2004 |
| ES | 2152429 | 9/1995 |
| FR | 2536657 | 11/1983 |
| FR | 2 536 657 A | 6/1984 |
| FR | 2838643 | 8/2002 |
| GB | 1249742 | 8/1969 |
| JP | 61-221113 | 10/1986 |
| JP | 11-508533 | 7/1999 |
| JP | WO0166074 | 9/2001 |
| JP | 2004-010576 | 1/2004 |
| JP | 2004-513142 | 4/2004 |
| JP | 4143542 | 9/2004 |
| JP | 10-504528 | 2/2010 |
| JP | 10-506629 | 3/2010 |

(Continued)

OTHER PUBLICATIONS

Amaechi et al., The influence of xylitol and fluoride on dental erosion in vitro, Archives of Oral Biology, 1998, 43, pp. 157-161.*

(Continued)

*Primary Examiner* — Frederick Krass
*Assistant Examiner* — Tracy Liu
(74) *Attorney, Agent, or Firm* — William R. Marjarian; Nora L. Stein (57) ABSTRACT

A dentifrice composition is described for combating dental erosion and/or tooth wear comprising a fluoride ion source and a silica dental abrasive, the dentifrice having a Relative Dentine Abrasivity (RDA) value from 20 to 60 and a pH in the range of 6.5 to 7.5 and being free of an orthophosphate buffer or a water soluble salt of a $C_{10-18}$ alkyl sulfate.

5 Claims, 4 Drawing Sheets

(56)  References Cited

FOREIGN PATENT DOCUMENTS

| WO | WO9207547 | | 5/1992 |
|---|---|---|---|
| WO | WO9311738 | | 12/1992 |
| WO | WO9325184 | | 6/1993 |
| WO | WO9415579 | | 7/1994 |
| WO | WO9632090 | | 10/1996 |
| WO | WO0215809 | | 2/2002 |
| WO | WO03055459 | | 7/2003 |
| WO | WO2004/016237 | | 2/2004 |
| WO | WO2004012693 | | 2/2004 |
| WO | WO2004/054529 | * | 7/2004 |
| WO | WO 2005067876 A1 | * | 7/2005 |

OTHER PUBLICATIONS van Rijkom et al. Erosion-inhibiting effect of sodium fluoride and titanium tetrafluoride treatment in vitro. (2003). Eur J Oral Sci. pp. 253-257.*
WO95/33441 corresponds to JP10-504528.
WO 96/09809 corresponds to JP10-506629.
WO96/09809 (A1) corresponds to ES2152429.
WO02/38119 (A1) corresponds to JP2004-513142.
EP1459733 (A1) corresponds to JP4143542.
S. Chunmuang, et al.: Effect of Xylitol and Fluoride on Enamel Erosion in vitro, Journal of Oral Science, vol. 49, No. 4, 293-297, 2007.
R. Sorvari, et al: Effect of Fluoride Varnish and Solution on Enamel Erosion in vitro, Basic Sciences, Caries Res, 1994; 28:227-232.

* cited by examiner

ALKYL SULFATE FREE AND ORTHOPHOSPHATE FREE DENTIFRICE COMPOSITION COMPRISING FLUORIDE SOURCE AND A SILICA DENTAL ABRASIVE

This application is a 371 of International Application No. PCT/EP2006/002665, filed 17 Mar. 2006.

FIELD OF THE INVENTION

The present invention relates to oral care compositions for combating (ie preventing, inhibiting and/or treating) dental erosion and/or tooth wear.

BACKGROUND OF THE INVENTION

Tooth mineral is composed predominantly of calcium hydroxyapatite, $Ca_{10}(PO_4)_6(OH)_2$, which may be partially substituted with anions such as carbonate or fluoride, and cations such as Zn and Mg. Tooth mineral may also contain non-apatitic mineral phases such as octacalcium phosphate and calcium carbonate.

Tooth loss may occur as a result of dental caries, which is a multifactorial disease where bacterial acids such as lactic acid produce sub-surface demineralisation that does not fully remineralise, resulting in progressive tissue loss and eventually cavity formation. The presence of a plaque biofilm is a prerequisite, and acidogenic bacteria such as *S. mutans* may become pathogenic when levels of easily fermentable carbohydrate, such as sucrose, are elevated for extended periods of time.

Even in the absence of disease, loss of dental hard tissues can occur as a result of acid erosion and/or physical wear; these processes are believed to act synergistically. Exposure of the dental hard tissues to acid causes demineralisation, resulting in surface softening and a decrease in mineral density. Under normal physiological conditions, demineralised tissues self-repair through the remineralising effects of saliva. Saliva is supersaturated with respect to calcium and phosphate, and in healthy individuals saliva secretion serves to wash out the acid challenge, and raises the pH so as to alter the equilibrium in favour of mineral deposition.

Dental erosion is a surface phenomenon that involves demineralisation, and ultimately complete dissolution of the tooth surface by acids that are not of bacterial origin. Most commonly the acid will be of dietary origin, such as citric acid from fruit or carbonated drinks, phosphoric acid from cola drinks and acetic acid such as from vinaigrette. Dental erosion may also be caused by repeated contact with hydrochloric acid (HCl) produced by the stomach, which may enter the oral cavity through an involuntary response such as gastroesophageal reflux, or through an induced response as may be encountered in sufferers of bulimia.

Tooth wear is caused by attrition and/or abrasion. Attrition occurs when tooth surfaces rub against each other, a form of two-body wear. An often dramatic example is that observed in subjects with bruxism, a grinding habit where the applied forces are high, and is characterised by accelerated wear, particularly on the occlusal surfaces. Abrasion typically occurs as a result of three-body wear and the most common example is that associated with brushing with a toothpaste. In the case of fully mineralised enamel, levels of wear caused by commercially available toothpastes are minimal and of little or no clinical consequence. However, if enamel has been demineralised and softened by exposure to an erosive challenge, the enamel becomes more susceptible to tooth wear. Dentine is much softer than enamel and consequently is more susceptible to wear. Subjects with exposed dentine should avoid the use of highly abrasive toothpastes, such as those based on alumina. Again, softening of dentine by an erosive challenge will increase susceptibility of the tissue to wear.

Dentine is a vital tissue that in vivo is normally covered by enamel or cementum depending on the location i.e. crown versus root respectively. Dentine has a much higher organic content than enamel and its structure is characterised by the presence of fluid-filled tubules that run from the surface of the dentine-enamel or dentine-cementum junction to the odontoblast/pulp interface. It is widely accepted that the origins of dentine hypersensitivity relate to changes in fluid flow in exposed tubules, the hydrodynamic theory, that result in stimulation of mechanoreceptors thought to be located close to the odontoblast/pulp interface. Not all exposed dentine is sensitive since it is generally covered with a smear layer, an occlusive mixture comprised predominantly of mineral and proteins derived from dentine itself, but also contains organic components from saliva. Over time, the lumen of the tubule may become progressively occluded with mineralised tissue. The formation of reparative dentine in response to trauma or chemical irritation of the pulp is also well documented. Nonetheless, an erosive challenge can remove the smear layer and tubule "plugs" causing outward dentinal fluid flow, making the dentine much more susceptible to external stimuli such as hot, cold and pressure. As previously indicated, an erosive challenge can also make the dentine surface much more susceptible to wear. In addition, dentine hypersensitivity worsens as the diameter of the exposed tubules increases, and since the tubule diameter increases as one proceeds in the direction of the odontoblast/pulp interface, progressive dentine wear can result in an increase in hypersensitivity, especially in cases where dentine wear is rapid.

Loss of the protective enamel layer through erosion and/or acid-mediated wear will expose the underlying dentine, and are therefore primary aetiological factors in the development of dentine hypersensitivity.

It has been claimed that an increased intake of dietary acids, and a move away from formalised meal times, has been accompanied by a rise in the incidence of dental erosion and tooth wear. In view of this, oral care compositions which help prevent dental erosion and tooth wear would be advantageous.

Oral care compositions generally contain a source of fluoride ions for promoting remineralisation of teeth and for increasing the acid resistance of dental hard tissues. To be effective the fluoride ions must be available for uptake into the dental hard tissues being treated. However some components of dentifrices such as silica abrasives can interact with and thereby decrease the amount of freely available fluoride ions.

One solution to this problem is suggested in U.S. Pat. No. 4,340,583 (Huber) which describes a toothpaste composition comprising a source of fluoride ions formulated with a specially treated silica abrasive that has good fluoride ion compatibility. These compositions have a pH in the range of 4 to 8, preferably 6.5 to 7.5 and may advantageously contain a soluble phosphate pellicle film penetration agent, a preferred example being an orthophosphate salt. Example 11 describes a low abrasive level toothpaste containing, as surfactant, a sodium alkyl sulphate.

Another solution is suggested in WO 01/66074 (Colgate) which recommends that the fluoride source should be stored at alkaline pH (to prevent interaction with a silica abrasive which may occur at acidic pH) but delivered at an acidic pH so as to enhance the uptake of the fluoride ions into the tooth enamel. This is achieved by the use of a dual component dentifrice, one phase being alkaline and containing the fluoride ions, the other phase being acidic and containing phosphate ions, which on mixing prior to use, provides an acidic phosphate fluoride composition (pH 4 to 6).

WO 04/012693 (Colgate) describes a dental composition having heightened desensitisation as well as heightened tooth fluoridation and remineralisation which is apparently achieved by combining a fluoride ion with a potassium salt, the composition having a pH in the range 7.5 to 9 and being buffered with an alkali metal phosphate salt.

SUMMARY OF THE INVENTION

The present invention provides a dentifrice composition for combating the increasingly prevalent problem of dental erosion and/or tooth wear which composition comprises a fluoride ion source and a silica dental abrasive, the dentifrice having a Relative Dentine Abrasivity (RDA) value from 20 to 60 and a pH in the range 6.5 to 7.5 and being free of an orthophosphate buffer or a water-soluble salt of a $C_{10-18}$ alkyl sulphate.

The pH referred to is that measured when the dentifrice composition is slurrried with water in a 1:3 weight ratio of the composition to water.

Compositions of the present invention are particularly beneficial in combating dental erosion since not only are they able to harden and thereby protect teeth from an acidic erosive challenge but also are able to reharden enamel softened by an acidic erosive challenge.

Furthermore, because of their low abrasivity, substantially neutral pH and absence of a powerful $C_{10-18}$ alkyl sulphate surfactant, such as sodium lauryl sulphate, commonly used in oral compositions, the compositions of the present invention do not exacerbate the problems associated with dental erosion and tooth wear.

Compositions of the present invention therefore have the advantage in effectively remineralising and strengthening teeth, thereby providing protection from and treatment for dental erosion and/or tooth wear.

Compositions of the present invention are also of use in the prophylaxis and treatment of dental caries and/or dental hypersensitivity.

DETAILED DESCRIPTION OF THE INVENTION

Suitable sources of fluoride ions for use in the compositions of the present invention include an alkali metal fluoride such as sodium fluoride, an alkali metal monofluorophosphate such a sodium monofluorophosphate, stannous fluoride, or an amine fluoride in an amount to provide from 25 to 3500 pm of fluoride ions, preferably from 100 to 1500 ppm. A preferred fluoride source is sodium fluoride, for example the formulation may contain 0.1 to 0.5% by weight of sodium fluoride, eg 0.205% by weight (equating to 927 ppm of fluoride ions), 0.2542% by weight (equating to 1150 ppm of fluoride ions) or 0.315% by weight (equating to 1426 ppm of fluoride ions).

Suitably the compositions of the present invention do not include a calcium salt which can reduce the availability of free fluoride ions.

Examples of suitable silica dental abrasives include those marketed under the following trade names Zeodent, Sident, Sorbosil or Tixosil by Huber, Degussa, Ineos and Rhodia respectively. The silica abrasive should be present in an amount sufficient to ensure the RDA of the dentifrice is between 20 and 60, preferably between 25 and 50 and more preferably between 25 and 40 to ensure adequate cleaning of teeth by the dentifrice whilst not promoting abrasion of teeth, especially teeth suffering from dental erosion or having been softened by an acidic challenge.

The silica abrasive is generally present in an amount up to 15% by weight of the total composition, for example from 2 to 10% by weight, and preferably at least 5% for example from 5 to 7% by weight, especially 6% by weight of the total composition. Reducing the level of silica abrasive has the advantage of not only lowering the abrasivity of the dentifrice but also minimising any interaction of the abrasive with fluoride ions thereby increasing the availability of free fluoride ions.

Suitable surfactants for use in the present invention include amphoteric surfactants for example, long chain alkyl betaines, such as the product marketed under the tradename 'Empigen BB' by Albright & Wilson, and preferably long chain alkyl amidoalkyl betaines, such as cocamidopropylbetaine, or low ionic surfactants such as sodium methyl cocoyl taurate, which is marketed under the trade name Adinol CT by Croda, or mixtures thereof. An amphoteric surfactant can be used alone as sole surfactant or can be combined with a low ionic surfactant.

Suitably, the surfactant is present in the range 0.1 to 10%, preferably 0.1 to 5% and more preferably 0.5 to 1.5% by weight of the total composition.

The pH of the dentifrice compositions is in the range 6.5 to 7.5, suitably from 6.8 to 7.2, for example 7.1 and can be adjusted by the incorporation of a base such as sodium hydroxide. Contrary to the teaching of the above-noted Colgate patent applications an orthophosphate buffer is to be avoided as its inclusion reduces the fluoride uptake into enamel.

In order to treat dental hypersensitivity the dentifrice composition of the present invention suitably further comprises a desensitising amount of a desensitising agent. Examples of desensitising agents include a tubule blocking agent or a nerve desensitising agent and mixtures thereof, for example as described in WO 02/15809 (Block). Preferred desensitising agents include a strontium salt such as strontium chloride, strontium acetate or strontium nitrate or a potassium salt such as potassium citrate, potassium chloride, potassium bicarbonate, potassium gluconate and especially potassium nitrate.

A desensitising amount of a potassium salt is generally between 2 to 8% by weight of the total composition, for example 5% by weight of potassium nitrate can be used.

The presence of potassium nitrate advantageously may provide an enhanced stain removal effect, which is of particular benefit for low abrasivity formulations, which otherwise might be expected to have relatively low cleaning performance.

Unlike many prior disclosed desensitising compositions containing a potassium salt (for example EP278744 (Unilever), WO 93/25184 (Procter & Gamble) and EP 1040819 (Pfizer), the compositions of the present invention do not contain sodium lauryl sulphate, which, whilst it has good detergent and cleaning properties, can cause the formation of an insoluble potassium lauryl sulphate precipitate.

The compositions of the present invention may further comprise an antierosion agent, for example a polymeric mineral surface active agent as described in WO 04/054529 (Procter & Gamble).

Compositions of the present invention will contain appropriate formulating agents such as thickening agents, humectants, flavouring agents, sweetening agents, opacifying or colouring agents, preservatives and water, selected from those conventionally used in the oral hygiene composition art for such purposes.

Suitable thickening agents include, for instance, nonionic thickening agents such as, for example, (C1-6)alkylcellulose ethers, for instance methylcellulose; hydroxy(C1-6)alkylcellulose ethers, for instance hydroxyethylcellulose and hydroxy propylcellulose; (C2-6)alkylene oxide modified (C1-6)alkylcellulose ethers, for instance hydroxypropyl methylcellulose; and mixtures thereof. Other thickening agents such as natural and synthetic gums or gum like material such as Irish Moss, xanthan gum, gum tragacanth, sodium carboxymethylcellulose, polyvinyl pyrrolidone, starch and thickening silicas may also be used. Preferably the thickening agent is mixture of a thickening silica and xanthan gum.

Advantageously the thickening agent is present in the range 0.1 to 30%, preferably 1 to 20%, more preferably 5 to 15% by weight of the total composition.

Suitable humectants for use in compositions of the invention include for instance, glycerin, xylitol, sorbitol, propylene glycol or polyethylene glycol, or mixtures thereof; which humectant may be present in the range from 10 to 80%, preferably 20 to 60%, more preferably 25 to 50% by weight of the total composition.

A preferred opacifying agent is titanium dioxide which may be present in the range 0.05 to 2%, preferably 0.075 to 0.2%, for example 0.1% by weight of the total composition. This amount enhances the visual appearance of the composition.

The compositions according to the present invention may be prepared by admixing the ingredients in the appropriate relative amounts in any order that is convenient and thereafter and if necessary adjusting the pH to give the final desired value.

The present invention also provides a method of combating dental erosion and/or tooth wear which comprises applying an effective amount of a composition of the present invention to an individual in need thereof. Such a composition also has benefit in the prophylaxis and treatment of dental caries and/or dental hypersensitivity (especially if it further contains a desensitising agent as hereinbefore described).

The invention is further illustrated by the following Examples.

| Dentifrice Formulation Raw Material | Example 1 % w/w | Example 2 % w/w | Example 3 % w/w |
|---|---|---|---|
| Sorbitol 70% solution - humectant | 30.000 | 30.000 | 32.000 |
| Abrasive silica | 6.000 | 6.000 | 6.000 |
| Thickening silica | 12.000 | 12.000 | 12.000 |
| Glycerin - humectant | 8.000 | 8.000 | 9.000 |
| Polyethylene glycol - humectant | 3.000 | 3.000 | 3.000 |
| Cocoamidopropylbetaine - surfactant | 1.200 | 1.200 | 1.200 |
| Xanthan gum - thickener | 0.800 | 0.800 | 1.000 |
| Titanium dioxide - opacifier | 0.100 | 0.100 | 0.100 |
| Potassium Nitrate - active | 5.000 | 5.000 | 0.000 |
| Sodium Fluoride - active | 0.315 | 0.2542 | 0.315 |
| Flavour oil | 1.100 | 1.100 | 1.100 |
| Saccharin sodium - sweetener | 0.300 | 0.300 | 0.300 |
| Sodium Hydroxide - pH adjuster | 0.082 | 0.082 | 0.082 |
| Water | To 100 | To 100 | To 100 |
| pH | 7.1 | 7.1 | 7.1 |

The following methods can be used to assess fluoride availability, fluoride uptake into enamel, acid protection efficacy, abrasivity, and cleaning power of the dentifrices of the present invention.

Example 4

Fluoride Uptake and Acid Protection

This example describes studies comparing the fluoride availability, fluoride uptake into enamel and the acid protection efficacy (assessed using a remineralization/demineralization cycling study) of compositions of the present invention with commercially available fluoride dentifrices as outlined in Table 1.

Fluoride Availability Studies

Samples were prepared by homogenization for 10 minutes, 1 part test dentifrice with 3 parts (w/w) distilled water. The pH of the slurries were measured prior to centrifugation at ca. 10,000 rpm to obtain a supernatant. The supernatants were diluted with water such that the range of the working standard bracketed the concentration of the fluoride ion. These solutions were analyzed by Dionex® Ion Chromatography with suppressed conductivity detection. Analyte concentrations were determined by external standardization.

The fluoride availability and pH of the various test products is summarized in Table I. These NaF dentifrices all exhibited good fluoride availability.

TABLE I

Available Fluoride and pH

| Product | Pack fluoride label and source | Fluoride availability (ppm) | pH (1:3) |
|---|---|---|---|
| Fluoride free dentifrice | none | <1 ppm | 7.1 |
| Crest Cavity Protection | 1100 ppm NaF | 951 | 7.3 |
| Crest Sensitive Original | 1100 ppm NaF | 900 | 9.1 |
| Enamel Care Natural Whitening | 1100 ppm NaF | 849 | 8.6 |
| Dentifrice of Example 2 | 1150 ppm NaF | 953 | 7.1 |

Enamel Fluoride Uptake (EFU)

The EFU test procedure was based on Procedure 40 described in the United States Food and Drug Administration (FDA) testing procedures. In the present case, the incipient lesion was formed using 0.1M lactic acid pH 5.0 containing 0.2% w/v polyacrylic acid (Carbopol 907) that was 50% saturated with hydroxyapatite.

Sound, upper, central, human incisors were selected and cleaned of all adhering soft tissue. A core of enamel 3 mm in diameter was prepared from each tooth by cutting perpendicular to the labial surface with a hollow-core diamond drill bit. This was performed under water to prevent overheating of the specimens. Each specimen was embedded in the end of a plexiglass rod (¼" diameter×2" long) using methylmethacrylate. The excess acrylic was cut away exposing the enamel surface. The enamel specimens were polished with 600 grit wet/dry paper and then with microfine Gamma Alumina.

Each enamel specimen was then etched by immersion into 0.5 ml of 1M perchloric acid ($HClO_4$) for 15 seconds under stirring. A sample of each solution was then buffered with total ionic strength adjustment buffer (TISAB—Orion Research Inc., Cambridge, Mass.) to a pH of 5.2 (0.25 ml sample, 0.5 ml TISAB and 0.25 ml 1N sodium hydroxide) and the fluoride content determined by comparison to a similarly prepared standard curve (1 ml std and 1 ml TISAB). These data reflect the indigenous fluoride level of each specimen prior to treatment.

The specimens were once again ground and polished as described previously. An incipient lesion was formed in each enamel specimen by immersion into a 0.1M lactic acid/0.2% Carbopol 907 solution for 24 hours at room temperature. These specimens were then rinsed well with distilled water and stored in a humid environment until used.

Specimens were treated by immersion in 25 ml of the relevant 1 part dentifrice and 3 parts (w/w) distilled water slurry supernatant, with constant stirring (350 rpm), for 30 minutes. After rinsing in deionised water, the surface layer was removed using a 15 second 1M $HClO_4$ etch as outlined previously and the fluoride content determined. The pre-treatment fluoride (indigenous) level of each specimen was then subtracted from the post-treatment value to determine the change in enamel fluoride content attributable to the test treatment. Statistical analyses were performed with a one-way analysis of variance model. Where significant differences were indicated, the individual means were analyzed by the Student Newman-Keuls (SNK) test.

The results of EFU studies conducted on the dentifrice of Example 2 and a variety of commercially available pastes are summarised in Table II. Of the products tested, the dentifrice of Example 2 of the present invention gave a statistically superior EFU, despite all the formulations having the same fluoride source and a similar fluoride availability.

TABLE II

In Vitro Fluoride Uptake Study

| Product Tested | Mean Fluoride Uptake* (ppm) | Stat Sig† |
|---|---|---|
| Fluoride-free dentifrice | 8 ± 4 | a |
| Crest Sensitive Original | 758 ± 18 | b |
| Crest Cavity Protection | 1191 ± 33 | c |
| Enamel Care Natural Whitening | 1496 ± 42 | d |
| Dentifrice of Example 2 | 1972 ± 91 | e |

*Means (n = 12) ± standard error of mean
†Values with different letter designations are statistically different (p < 0.05) as determined by Student Newman-Keuls analysis.

In Vitro Remineralization/Demineralization Studies.

The purpose of this study was to determine the efficacy of fluoride dentifrices to promote enamel fluoride uptake and reduce subsequent demineralization under dynamic conditions simulating exposure to dietary acids. An acidic buffer of 1% w/v citric acid monohydrate adjusted to pH 3.8 with NaOH was chosen to match orange juice in terms of pH and total titratable acidity.

Mounted enamel specimens (3 mm diameter, n=18) were prepared according to the method described earlier for EFU. They were used as sound or slightly eroded. SMH was determined using a Vickers microindenter at a load of 200 g for 15 seconds. The average specimen hardness, expressed as Vickers hardness number (VHN), was determined from four indentations on the surface of each specimen.

The acid resistance of the enamel was determined by individually placing the specimens into 5.0 ml of stirred citric acid buffer for 11 minutes. The specimens were then immersed into 10 ml of the unstirred citric acid buffer for an additional 20 minutes. The SMH was then remeasured, and the acid-softened specimens distributed into groups based on the post-erosion SMH. A 50:50 mixture of pooled human saliva and mucin-containing artificial saliva buffer (M-ASB) was used as the remineralization medium in all cycling experiments. The M-ASB comprised of 2.20 g/l gastric mucin, 0.381 g/l sodium chloride, 0.213 g/l calcium chloride dehydrate, 0.738 g/l potassium dihydrogen orthophosphate and 1.114 g/l potassium chloride. Wax-stimulated human saliva was collected from at least five individuals for pooling and refrigerated until used. Saliva samples were then pooled with vigorous stirring prior to distribution (7.5 ml saliva+7.5 ml M-ASB) into 30 ml treatment beakers. Fresh saliva/mineral mix was used each day.

During the treatment period, the specimens were immersed in dentifrice slurries to simulate daily brushing. The slurries were prepared by adding 5.0 g of dentifrice to 10 g of the fresh saliva/mineral mix solution in a beaker with a magnetic stirrer. A fresh slurry was prepared just prior to each treatment. The daily cycling regimen comprised 5×2 min acid challenges and 3×2 min treatment periods. After the treatments, the specimens were rinsed with running distilled water and then replaced back into the saliva/M-ASB. The SMH was remeasured after 10 and 20 days cycling. The treatment schedule used for this experiment is given as shown below:

| a. | 8:00-8:02 | Dentifrice treatment 1* |
|---|---|---|
| b. | 8:02-10:00 | Saliva treatment |
| c. | 10:00-10:02 | Acid buffer challenge 1 |
| d. | 10:02-11:00 | Saliva treatment |
| e. | 11:00-11:02 | Acid buffer challenge 2 |
| f. | 11:02-12:00 | Saliva treatment |
| g. | 12:00-12:02 | Dentifrice treatment 2 |
| h. | 12:02-13:00 | Saliva treatment |
| i. | 13:00-13:02 | Acid buffer challenge 3 |
| j. | 13:02-14:00 | Saliva treatment |
| k. | 14:00-14:02 | Acid buffer challenge 4 |
| l. | 14:02-15:00 | Saliva treatment |
| m. | 15:00-15:02 | Acid buffer challenge 5 |
| n. | 15:02-16.30 | Saliva treatment |
| o. | 16:30-16.32 | Dentifrice treatment 3 |
| p. | 16:32-8:00 | Saliva treatment |
| q. | Back to (a) | |

*On day 1, this treatment was omitted; the test began with one hour in saliva to permit pellicle development prior to any treatments.

At the end of the 20-day treatment regimen, the fluoride content of each enamel specimen was determined using the microdrill technique to a depth of 100 μm. Fluoride data were calculated as weight of fluoride per unit sampled as μg $F/cm^3$.

Statistical analyses were performed with a one-way analysis of variance model. Where significant differences were indicated, the individual means were analyzed by the Student Newman-Keuls (SNK) test.

The results of these studies are summarized in Table III.

TABLE III

SMH and Fluoride uptake following Remineralization/Demineralization

| | VHN*† | | | | F Uptake*† |
|---|---|---|---|---|---|
| Product Tested | Baseline | Initial acid challenge | 10 days cycling | 20 days cycling | µg F/cm$^3$ 20 days cycling |
| Fluoride free dentifrice | 320 ± 3$^a$ | 264 ± 5$^a$ | 217 ± 4$^a$ | 214 ± 4$^a$ | 284 ± 33$^a$ |
| Crest Cavity Protection | 324 ± 3$^a$ | 265 ± 5$^a$ | 256 ± 6$^b$ | 246 ± 5$^b$ | 337 ± 31$^a$ |
| Dentifrice of Example 2 | 326 ± 3$^a$ | 268 ± 3$^a$ | 280 ± 4$^c$ | 270 ± 5$^c$ | 479 ± 24$^b$ |

*Means (n = 18) ± standard error of mean
†In columns, values with different letter designations are statistically different (p < 0.05) as determined by Student Newman-Keuls analysis The SMH microhardness (VHN) data showed that both the dentifrice of Example 2 and Crest Cavity Protection conferred statistically significant levels of protection against acid-mediated softening of the enamel specimens relative to the fluoride-free control at 10 and 20 days. However, the dentifrice of Example 2 conferred statistically superior protection versus Crest Cavity Protection at 10 and 20 days (Table III). Furthermore, the dentifrice of Example 2 also delivered a net increase in SMH of the lesions over the study period. The fluoride uptake data indicated that the dentifrice of Example 2 was able to promote more fluoride uptake than the Crest Cavity Protection. Although a numerical increase in fluoride uptake was observed for the Crest Cavity Protection, this was not significant over the fluoride-free placebo.

These studies demonstrate that not only was the dentifrice of Example 2 statistically superior to Crest Cavity Protection in protecting the enamel from further surface softening, but in this particular study the lesion was rehardened. The degree of acid protection was positively correlated with the extent of fluoride uptake by the specimens which suggests that the more effective delivery of fluoride from the dentifrice of Example 2 results in enhanced protection from acid demineralization and promotes more effective remineralization.

In summary these in vitro studies demonstrate that a composition of the present invention provides superior levels of protection against repeated insult by a dietary acid challenge.

Example 5

In Vitro Hard Tissue Abrasion Studies

Radioactive dentine and enamel abrasion studies were performed as previously reported in the literature (Hefferen, J. Dent. Res. 55 563-573, 1976 and Hefferen et al, J. Dent. Res. 63 1176-1179, 1984).

The dentine or enamel specimens were placed in a neutron flux resulting in the controlled formation of radioactive $^{32}$P within the specimens. The specimens were then mounted in methylmethacrylate so they would fit in a V-8 cross-brushing machine. Dentine specimens were brushed for 1500 strokes, enamel specimens 5000 strokes, as a precondition run using slurry consisting of 10 g dicalcium pyrophosphate in 50 ml of a 0.5% carboxymethylcellulose (CMC) glycerin solution. The slurry was also used as the internal reference standard. The brushes used were those specified by the American Dental Association (ADA), and brush load was 150 g.

Following the precondition run, the test was performed using a 150 g brush load with 1500 strokes for dentine, or 5000 strokes for enamel in a sandwich design in which each test material slurry (25 g of dentifrice plus 40 ml water) was flanked by the reference material slurries (10 g/50 ml 0.5% CMC). The water control consisted of 50 ml water only. As brushing takes place particles are abraded from the enamel or dentine surfaces into the brushing slurry. Aliquots of the slurries were diluted into scintillation media and the radioactivity determined using a scintillation counter, i.e. the loss of $^{32}$P from the specimens.

The net count of the pre and post reference material against each of the test slurries was then calculated and averaged. The ratio of the count for the test slurries against the reference average is used in the calculation of the RDA or REA. The ratio of test slurry against reference is multiplied by a constant of 100 to produce the RDA scale and 10 for the REA scale.

Results obtained for the in vitro abrasion of the dentifrice of Example 2 and a variety of commercially available dentifrices are summarized in Tables IV and V for RDA and REA respectively. The dentifrice of Example 2 exhibited the lowest RDA and REA of the dentifrices under test, indicating a very low hard tissue abrasion.

TABLE IV

In Vitro Relative Dentine Abrasion Study

| Product Tested | RDA* |
|---|---|
| Enamel Care Natural Whitening | 153.4 ± 8.4 |
| Crest Cavity Protection | 106.1 ± 4.6 |
| Crest Sensitive Original | 102.3 ± 4.8 |
| Dentifrice of Example 2 | 34.7 ± 1.6 |
| Abrasive free control dentifrice | 10.7 ± 1.5 |
| Water | 10.2 ± 0.8 |

*Means (n = 8) ± standard error of mean

TABLE V

In Vitro Relative Enamel Abrasion Study

| Product Tested | REA* |
|---|---|
| Crest Cavity Protection | 4.34 ± 0.51 |
| Dentifrice of Example 2 | 2.58 ± 0.06 |
| Abrasive free control dentifrice | 1.12 ± 0.08 |

*Means (n = 8) ± standard error of mean

Example 6

In Vitro Microhardness Studies

This example describes further studies indicating that compositions of the present invention can strengthen and harden dental enamel and can be used both to protect and to treat teeth at risk from dental erosion and tooth wear.

Citric acid monohydrate, magnesium chloride, calcium chloride dihydrate, potassium chloride, ammonium chloride, N-2-hydroxyethylpiperazine-N'-ethanethesulphonic acid (HEPES), sodium hydroxide and potassium hydroxide were obtained from Sigma-Aldrich (Dorset, UK). Potassium dihydrogen orthophosphate was obtained from VWR (Poole, UK). Stycast acrylic resin was obtained from Hitek Electronic Materials (Scunthorpe, UK). The composition of the artificial saliva employed was as follows: magnesium chloride (0.20 mM), calcium chloride dihydrate (1.0 mM), potassium dihydrogen orthophosphate (4.0 mM), HEPES (20.0 mM), potassium chloride (16.0 mM), ammonium chloride (4.5 mM). The pH was adjusted to 7.0 using potassium hydroxide (1.0 M).

Formulations tested are as described in Table VI.

TABLE VI

Formulation details for toothpastes tested in microhardness studies. Formulation pH refers to a 1:3 w/w paste slurry in deionised water (MFP: sodium monofluorophosphate, AmF: amine fluoride, NaF: sodium fluoride, SLS: sodium lauryl sulphate).

| Test product | Fluoride source, and concentration (ppm) | Abrasive system | Surfactant | Formulation pH |
|---|---|---|---|---|
| Dentifrice of Example 1 | NaF, 1426 | Silica | Cocoamidopropyl-betaine | 7.1 |
| Fluoride free control | N/A | Silica | Cocoamidopropyl-betaine | 7.1 |
| Elmex Sensitive | AmF, 1400 | Silica | SLS | 4.9 |
| Colgate Sensitive | MFP, 1500 | Silica | SLS | 7.0 |

Statistical Analysis

An analysis of variance was performed on the data, followed by comparisons between the individual treatments. The significance was set to $p<0.05$. Data was analysed using the program SAS, mixed procedure (SAS institute Inc., Cary, USA).

Preparation of Sound Enamel Specimens

Extracted human molars and premolars were stored in an aqueous solution of saturated thymol after removal of the roots and pulp. Prior to use, teeth were thoroughly rinsed and examined for evidence of damage. Sound enamel sections were cut from the buccal and lingual sides of the teeth using a diamond saw (Struers Minitom). The sections were mounted in acrylic resin and cured overnight. The specimens were then polished flat using 1200 and 2400 grit silicon carbide paper, before storing dry at 4° C. Specimens were rehydrated in deionised water for at least 60 minutes prior to use.

Microindentation

Specimen SMH was determined using a Struers Duramin-1 microhardness tester fitted with a Vickers diamond indentor. A load of 1.961N (200 g) was applied to the specimens, with a dwell time of 20 seconds. The SMH was expressed in terms of the Vickers Hardness Number (VHN), and the VHN of a specimen at each time point was based on the mean of six indents.

Citric Acid-Mediated Enamel Surface Softening

Baseline SMH of 24 sound enamel specimens was determined, and the specimens randomly assigned to one of four treatment groups (n=6). Each specimen was individually numbered and used as its own control. Specimens were immersed in one of four agitated toothpaste slurries prepared from deionised water (1:3) for 120 seconds. The specimens were then rinsed with deionised water and immersed in 1% citric acid (pH 3.75) for a total of 30 minutes. Specimens were removed at 10 minute intervals, and after rinsing in deionised water to remove residual acid, the SMH was determined.

Figure 1:
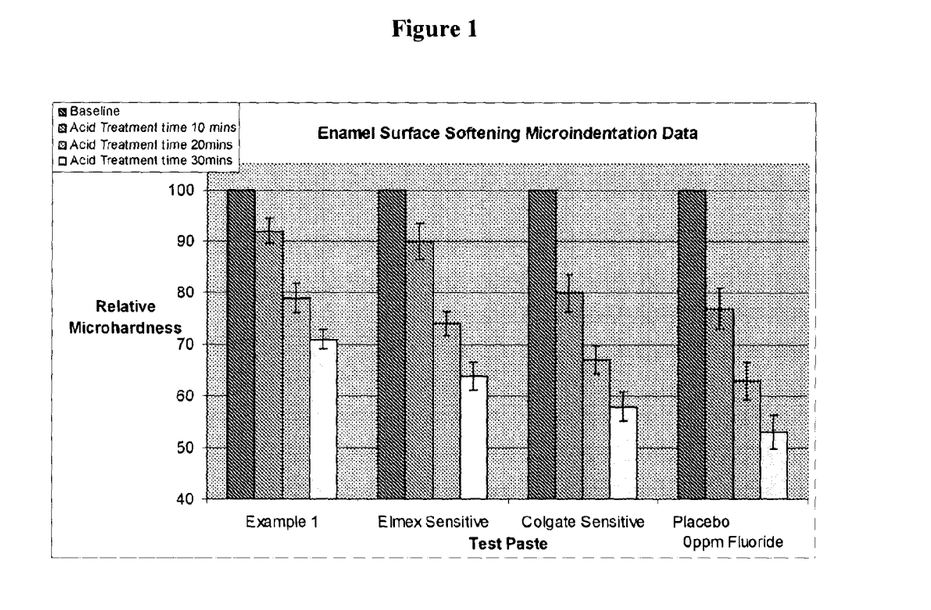
FIG. 1 depicts the effect on enamel surface microhardness (SMH) of a single 2 minute pre-treatment with a 1:3 paste slurry in deionised water prior to exposure to a 1.0% citric acid, pH 3.75 challenge.

The results of the enamel surface softening study are summarised in FIG. 1. The SMH values have been normalised relative to baseline. The degree of acid induced surface softening of specimens treated with the dentifrice of Example 1 and Elmex Sensitive was reduced to a statistically significant extent relative to the Colgate Sensitive and fluoride-free control treated specimens, at all time points. Inhibition of acid-mediated surface softening was statistically superior for the dentifrice of Example 1 versus Elmex Sensitive after 20 and 30 minutes, but not after 10 minutes. Inhibition of surface softening was statistically superior for Colgate Sensitive versus the fluoride-free control at the 20 and 30 minute time points, but not at 10 minutes.

In summary, the enamel surface softening model has demonstrated that a composition of the present invention is able to protect enamel from an erosive challenge and therefore is useful in providing protection against dental erosion and tooth wear.

Lesion Rehardening

Erosive lesions were prepared from 24 sound enamel specimens by immersing the specimens individually for 30 minutes in 10 ml of a 1.0% w/w solution of citric acid, pH 3.75. Baseline SMH was then determined before randomly assigning the specimens to one of four treatment groups (n=6). Again, each specimen was individually numbered and used as its own control. Specimens were immersed in one of the four agitated toothpaste slurries prepared from deionised water (1:3) for 120 seconds. The specimens were then rinsed with deionised water and placed into artificial saliva containing an aliquot of the corresponding toothpaste slurry to mimic in vivo carryover of the formulation.

Three separate studies were performed using progressively higher dilutions of the original paste formulations to simulate carryover concentrations present in saliva minutes and hours after toothpaste use. A dilution level of 1:1426 for the paste in the artificial saliva was chosen initially (study R1). This dilution resulted in a fluoride concentration of ca. 1 ppm in the saliva. The level of dilution was increased in subsequent experiments to give final concentrations of fluoride in the artificial saliva of ca. 0.04 and 0.02 ppm (study R2 and R3 respectively). Specimen rehardening was determined after 4, 24 and 48 hrs incubation in the modified artificial saliva. The results of the enamel rehardening studies, R1-R3, involving commercial pastes are summarised in FIGS. 2-4 respectively. The SMH values have again been normalised relative to baseline.

Figure 2:
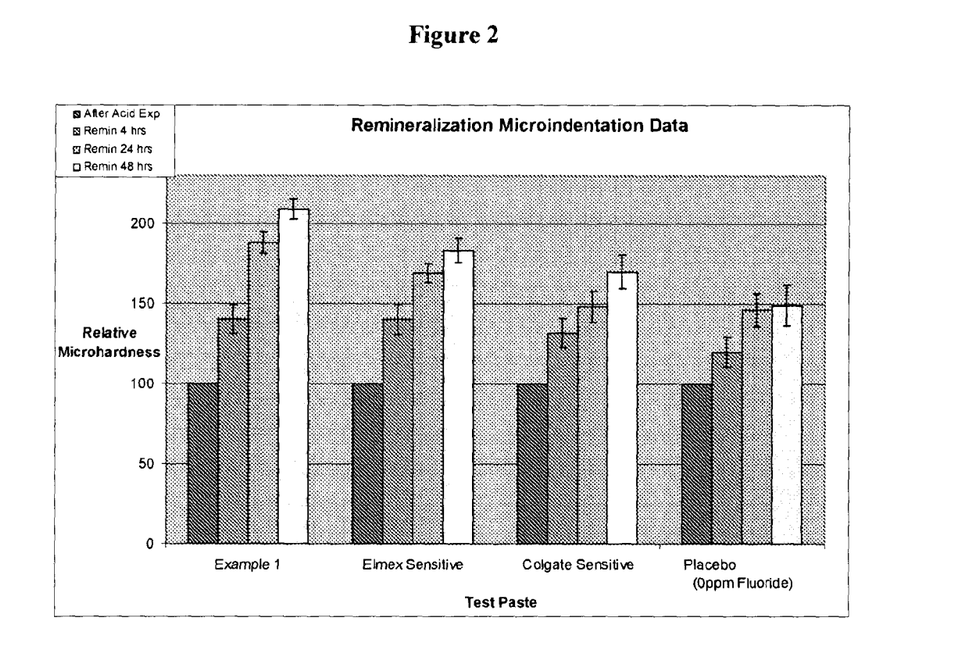
FIG. 2 depicts rehardening of enamel erosive lesions following a 2 minute treatment with a 1:3 paste slurry in deionised water, and subsequent incubation in artificial saliva modified with an aliquot of the relevant toothpaste to yield a final fluoride concentration of ca 1 ppm.

In study R1, where the artificial saliva contained fluoride at ca. 1 ppm, all treatment groups rehardened to a statistically significant extent versus baseline at all time points. All fluoride-based treatments conferred statistically superior rehardening relative to the fluoride-free control at 4 hours; numerical differences between the fluoride treatments were not statistically significant at this time point. However, at the 24 and 48 hr time points, the dentifrice of Example 1 treatment group exhibited statistically superior rehardening versus all other treatment groups. Elmex Sensitive was significantly superior to Colgate Sensitive and the fluoride-free placebo at 24 and 48 hrs. Colgate Sensitive was statistically superior to the fluoride-free control at 48 hrs, but not at 24 hrs.

Figure 3:
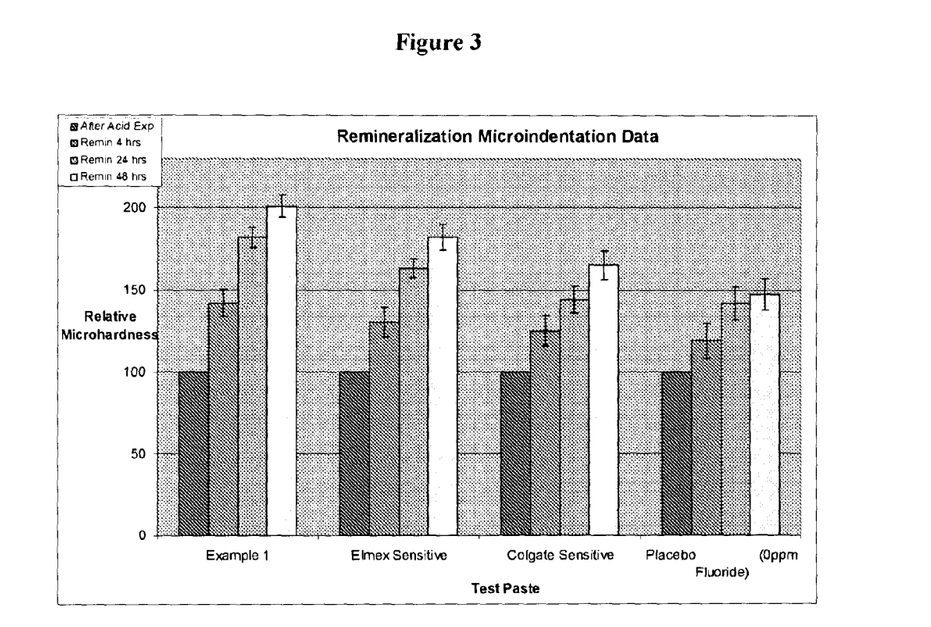
FIG. 3 depicts rehardening of enamel erosive lesions following a 2 minute treatment with a 1:3 paste slurry in deionised water, and subsequent incubation in artificial saliva modified with an aliquot of the relevant toothpaste to yield a final fluoride concentration of ca. 0.04 ppm.
Figure 4:
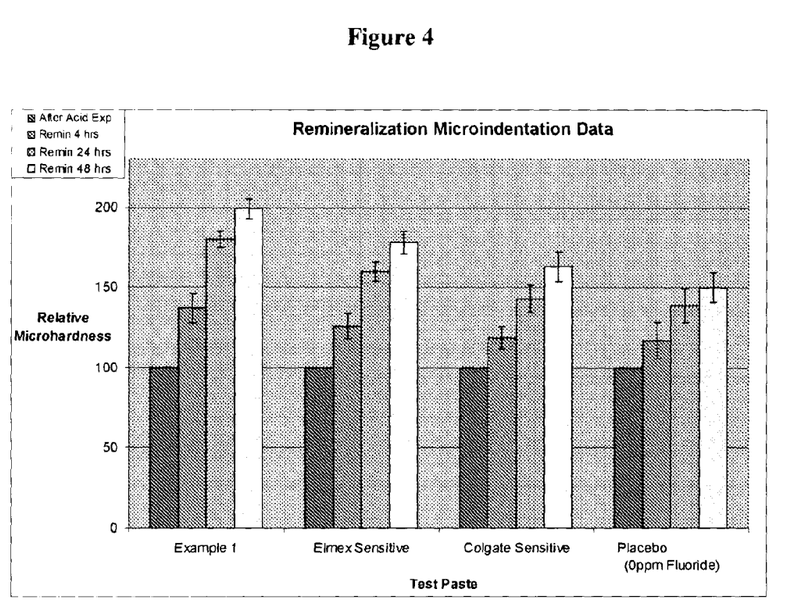
FIG. 4 depicts rehardening of enamel erosive lesions following a 2 minute treatment with a 1:3 paste slurry in deionised water, and subsequent incubation in artificial saliva modified with an aliquot of the relevant toothpaste to yield a final fluoride concentration of ca 0.02 ppm.

Data from studies R2 and R3 are summarised in FIGS. 3 and 4 respectively. The behavioural trends are similar to those observed in FIG. 2.

Again, all treatment groups rehardened the erosive lesions to a statistically significant extent versus baseline. The dentifrice of Example 1 treatment group exhibited statistically superior rehardening at all time points relative to Colgate Sensitive and the fluoride-free control, and was statistically superior to Elmex Sensitive at the 24 and 48 hr time points. No significant differences were observed between Elmex Sensitive, Colgate Sensitive and the fluoride-free control at 4 hrs, however Elmex Sensitive was statistically superior to both Colgate Sensitive and the fluoride-free control at the 24 and 48 hr time points. Colgate Sensitive was not statistically superior to the fluoride-free control at any time point.

The data displayed in FIGS. 2-4 clearly show that erosive lesions can be rehardened, and that rehardening is promoted by use of fluoride-containing toothpastes. The increase in enamel SMH is believed to occur as a result of lesion repair, during which new mineral is deposited onto the enamel surface and within the demineralised sub-surface.

Erosive lesions treated with the dentifrice of Example 1 and Elmex Sensitive, the two fluoride-containing pastes, rehardened to a statistically significant extent versus the fluoride-free placebo at all time points and in all three studies except R3 where the difference at 4 hr was not significant. Treatment with the dentifrice of Example 1 consistently led to greater rehardening of the lesions at the 24 and 48 hr time points than was observed with Elmex Sensitive. This trend was therefore independent of the level of fluoride added to the artificial saliva over the studied range. The rate of lesion repair was also relatively insensitive to the level of fluoride in the artificial saliva. This would suggest that the initial treatment is a key factor in determining the extent of subsequent rehardening. Treatment of the lesions with Colgate Sensitive led to directionally greater rehardening than was observed with the fluoride-free control paste. In this case the free fluoride level during the slurry treatment will be low, however there is an opportunity for MFP bound to the enamel surface to hydrolyse during its incubation in artificial saliva. In study R1, complete hydrolysis of the MFP present in the artificial saliva would be expected to yield at least 1 ppm free fluoride.

In summary, microhardness studies have shown that fluoride-containing toothpastes are capable of both inhibiting enamel surface softening by citric acid, and of promoting repair of enamel erosive lesions. In particular, the dentifrice of Example 1 used in the present study, which has high levels of available fluoride designed for enhanced uptake into dental enamel, advantageously exhibited a promising level of enamel protection and lesion repair.

Example 7

Stain Removal Efficacy

This example describes two different methods of comparing the stain removal performance of a composition of the present invention with several commercially available dentifrices: Elmex® Sensitive (Gabs, Switzerland), Sensodyne MultiCare® and Aquafresh Fresh'n'Minty®.

Pellicle Cleaning Ratio Methodology

The PCR uses cut, polished and acid-etched bovine enamel as substrate for build-up of a complex artificial stain incorporating dietary chromogens and chromogenic bacteria. All PCR testing was performed as described in Stookey et al., J. Dent. Res. 61: 1236-1239, 1982.

The PCR values determined for the dentifrice of Example 1 and Elmex® are given in Table VII:

TABLE VII

PCR values for Dentifrice of Example 1 and Elmex ® Sensitive

| Product | PCR value (mean + std error, n = 16) |
|---|---|
| Dentifrice of Example 1 | 46 ± 4 |
| Elmex ® Sensitive | 52 ± 5 |

The difference between these values was not statistically significant in terms of cleaning power.

Natural Extrinsic Stain Removal (NESR) Methodology

Bovine incisor crowns were cut, depulped, rinsed in deionised water and allowed to dry. An acrylic mounting solution was prepared by mixing 100 g of self-cure acrylic repair material powder with 40 g self-cure acrylic liquid (both from Bracon Ltd.). The resulting mixture was poured into bottle caps, 3.5 cm diameter by 1.5 cm deep (Ecotrin, Van Blarcom Closures). The teeth were pushed into the mixture during hardening in each cap and leveled to ensure a near-flat surface. All teeth were mounted centrally in the caps.

The mounted teeth were placed into machined slots in a 42-stage reciprocal action brushing machine using Oral B 40 Indicator toothbrushes, such that the brush traveled up and down the length of the tooth. The brushing rate was 100 cycles per minute at a brush loading of 100 g.

The teeth were pre-brushed for 10 minutes with a 1:3 w/w slurry of Macleans Milkteeth in deionised water to remove loose stain. The teeth were removed, rinsed in water and allowed to dry in air overnight.

The stain on the teeth was assessed using a Hunterlab Huntercolour LS6100 chromameter using the L* parameter of the CIE lab L*A*B* scale. Readings were taken at each of five evenly spaced points around each tooth. Teeth in the L* value range 50 to 90 after pre-brushing were randomised across treatment groups.

The stain removal performance of a test paste (A) can be determined relative to a benchmark control (B). For a two-product comparison of A vs. B, the teeth were randomly divided into two sets. In the first treatment phase, one set of teeth was brushed with a 1+1 w/w slurry of formulation A in deionised water for 30 minutes and the second set was brushed with formulation B in the same conditions. The teeth were washed and dried as above. The L* value was recorded and then the teeth underwent a second treatment phase. In this phase, the set previously treated with formulation A was treated with formulation B, and the set treated with formulation B was treated with formulation A. The teeth were washed, dried and the L* value measured as previously. Each treatment group consisted of 14 teeth, i.e. 28 per two-product comparison.

The relative stain removal efficacy of A and B was determined by comparing, for each treatment sequence, the amount of stain removed during the first treatment phase as a proportion of the total amount of stain removed by both treatment phases. That is, whether:

$$\Delta L^*(T1[A])/\Delta L^*(T1[A])+\Delta L^*(T2[B])$$

is statistically significantly different from (p<0.05, two-tailed student t-test):

$$\Delta L^*(T1[B])/\Delta L^*(T1[B]) + \Delta L^*(T2[A])$$

where T1 and T2 are treatment phases 1 and 2 respectively, and A and B are formulations A and B respectively. Values are expressed here as percentages and are constrained to be within the range 0-100%.

The NESR values determined for the dentifrice of Example 1 compared separately to Sensodyne MultiCare®, Aquafresh Fresh'n'Minty® and Elmex® Sensitive are given in Table VIII below:

TABLE VIII

NESR values for the dentifrice of Example 1 vs. commercial products

| Treatment | % Stain Removed by 1st brush (mean ± std. error, n = 14) | p-value |
|---|---|---|
| Dentifrice of Example 1 followed by Sensodyne MultiCare ® | 86 ± 2 | p = 0.0005 |
| Sensodyne MultiCare ® followed by Dentifrice of Example 1 | 71 ± 3 | |
| Dentifrice of Example 1 followed by Aquafresh Fresh'n'Minty ® | 92 ± 2 | p = 0.001 |
| Aquafresh Fresh'n'Minty ® followed by Dentifrice of Example 1 | 80 ± 2 | |
| Dentifrice of Example 1 followed by Elmex ® Sensitive | 42 ± 4 | p = 0.165 |
| Elmex ® Sensitive followed by Dentifrice of Example 1 | 32 ± 6 | |

Table VIII shows that the dentifrice of Example 1 removes more stain in the NESR model than either Sensodyne MultiCare® or Aquafresh Fresh'n'Minty®. Although not significant at the 5% level, the data also provide some evidence to suggest that it may outperform Elmex® Sensitive (42% stain removed by 1st brush with the dentifrice of Example 1 vs. 32% for Elmex®).

The stain removal performance of the dentifrice of Example 1 is high for a product having low abrasivity. In part this performance appears to be due to the presence of 5% $KNO_3$ in the formulation. It is possible that this effect arises from the relatively high solubility of calcium nitrate, that is, some of the calcium in stain is liberated into solution by the presence of nitrate ions, thereby weakening the stain matrix.

The invention claimed is:

1. A method of combating dental erosion and/or tooth wear which comprises applying to an individual in need thereof an effective amount of an aqueous dentifrice composition comprising:
    sodium fluoride in an amount from 1150 ppm to 3500 ppm of fluoride ions;
    0.1% to 5% by weight of cocamidopropyl betaine as the sole surfactant;
    2% to 10% by weight of a silica dental abrasive;
    2 to 8% by weight of potassium nitrate;
    the dentifrice having a Relative Dentine Abrasivity (RDA) value from 20 to 60 and a pH in the range 6.5 to 7.5, and wherein the composition is free of an orthophosphate buffer, a water-soluble salt of a $C_{10-18}$ alkyl sulphate a calcium salt and a further anti-erosion agent; and
    wherein the composition enhances fluoride uptake into the teeth and is able to harden and thereby protect teeth from an acidic erosive challenge and is able to reharden enamel softened by an acidic erosive challenge.

2. The method according to claim 1, wherein the RDA of the dentifrice is from 25 to 50.

3. The method according to claim 1, wherein the RDA of the dentifrice is from 25 to 40.

4. The method according to claim 1, wherein the pH is in the range 6.8 to 7.2.

5. The method according to claim 1, further comprising titanium dioxide as an opacifying agent in an amount from 0.05 to 2% by weight of the total composition.

* * * * *